United States Patent [19]

Yamatsu et al.

[11] Patent Number: 4,835,183
[45] Date of Patent: May 30, 1989

[54] METHOD OF TREATING CANCEROUS AND PRECANCEROUS CONDITIONS

[75] Inventors: Isao Yamatsu, Saitama; Yuichi Inai; Shinya Abe, both of Tokyo; Takeshi Suzuki, Abiko; Yoshikazu Suzuki, Ichinomiya; Osamu Tagaya, Gifu; Kouichi Suzuki, Kakamigahara; Kouichi Abe; Kouji Yamada, both of Tokyo, all of Japan

[73] Assignee: Eisai Co., Ltd., Tokyo, Japan

[21] Appl. No.: 451,318

[22] Filed: Dec. 20, 1982

Related U.S. Application Data

[62] Division of Ser. No. 260,870, May 6, 1981.

[30] Foreign Application Priority Data

Dec. 24, 1980 [JP] Japan .................. 65-182116

[51] Int. Cl.⁴ .................. A61K 31/22; A61K 31/20; A61K 31/16; A61K 31/12
[52] U.S. Cl. .................. 514/549; 514/560; 514/627; 514/675
[58] Field of Search .............. 424/312, 320, 318, 331, 424/260, 870; 514/549, 560, 627, 675

[56] References Cited

FOREIGN PATENT DOCUMENTS 545042 1/1979 Japan .

OTHER PUBLICATIONS

Caliezi et al., Helv. Chim. Acta., vol. 35, pp. 1649–1655 (1952).
Agri, Biol. Chem., vol. 34, No. 8, p. 1184 (1970).
Journal Chem. Soc. (London) (c) pp. 2154–2165, Davis et al.

*Primary Examiner*—Jerome D. Goldberg
*Attorney, Agent, or Firm*—Flynn, Thiel, Boutell & Tanis

[57] ABSTRACT

An anti-cancer agent which comprises a polyprenyl compound having the formula (I):

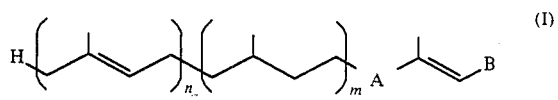

(I)

in which each of n and m is 0, 1 or 2, n+m is 0, 1 or 2, A is

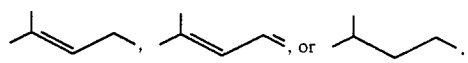

and B is

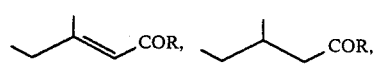

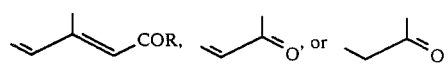

in which R represents the hydroxyl group, a lower alkoxy group, or

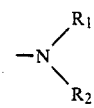

(wherein each of $R_1$ and $R_2$ is the hydrogen atom, a lower alkyl group or an aryl group)]; provided that R is a lower alkoxy or

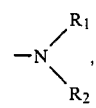

if n is 1, m is 0, A is

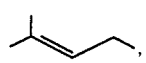

and B is

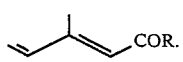

11 Claims, No Drawings

METHOD OF TREATING CANCEROUS AND PRECANCEROUS CONDITIONS

This is a division, of application Ser. No. 260,870 filed May 6, 1981.

This invention relates to an anti-cancer agent which comprises a polyprenyl compound having the formula (I):

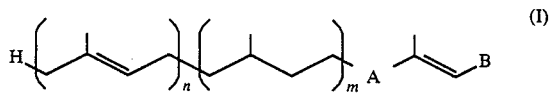

in which each of n and m is 0, 1 or 2, n+m is 0, 1 or 2, A is

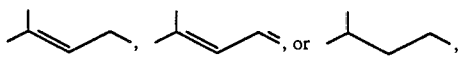

and B is

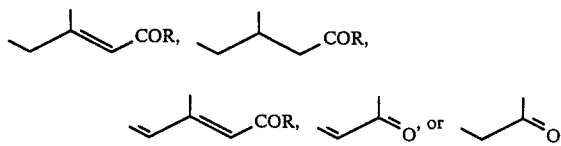

in which R represents the hydroxyl group, a lower alkoxy group, or

(wherein each of $R_1$ and $R_2$ is a hydrogen atom, a lower alkyl group or an aryl group); provided that R is lower alkoxy or

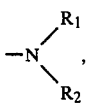

if n is 1, m is 0, A is

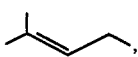

and B is

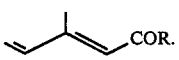

Examples of the lower alkoxy groups represented by R in the above-mentioned formula (I) include methoxy, ethoxy, i-propoxy, n-propoxy, t-butoxy and n-butoxy. Examples of the lower alkyl groups represented by $R_1$ and $R_2$ include methyl, ethyl, i-propyl, n-propyl, t-butyl and n-butyl, and examples of the aryl groups represented by $R_1$ and $R_2$ include phenyl and a phenyl group having substituent groups such as hydroxyl, a lower alkyl group or halogen. If R in the formula (I) is hydroxyl, the compound may be in the form of a salt such as sodium or potassium salt.

W. Bollag, et al. reported in Europ. J. Cancer. Vol. 10, p 731 (1974) that retinoides such as ethyl 9-(2,3,6-trimethyl-4-methoxyphenyl)-3,7-dimethyl-2,4,6,8-nonatetraenoate have anti-cancer activity. These retinoide comounds, however, are highly toxic, and further have problems such as causing hypervitaminosis of Vitamin A when administered.

The present invention provides an anti-cancer agent comprising polyprenyl compounds of the formula (I). The polyprenyl compounds of the formula (I) show remarkable anticancer activity and are highly safe compounds. For instance, these polyprenyl compounds do not cause hypervitaminosis of Vitamin A. Further, toxicities of the polyprenyl compounds of the formula (I) other than hypervitaminosis are also at low levels.

Moreover, the polyprenyl compounds of the formula (I) are of value as therapeutic agents for treatment of skin diseases with keratinization or treatment of allergic or inflammatory skin diseases, such as psoriasis, acne, acne vulgaris, Darier's disease, palmoplantar pustulosis, lichen plasnus, ichthyosis, erythroderma, pityriasis rubra pilasis, and keratosis senilis, as well as the therapeutic agents for treatment of cancer and precancerous conditions.

Some of the polyprenyl compounds of the formula (I) are already known. For instance, some polyprenyl compounds represented by the formula (I) are described in Japanese Patent Provisional Publication No. 54-5042, Helv. Chim. Acta., Vol. 35, p. 1649 (1952), Agr. Biol. Chem., Vol. 34, No. 8, p. 1184 (1970), and J. Chem. Soc., (C) p. 2154 (1966). However, there are no description about the anti-cancer activity of these compounds in these references.

Examples of the known polyprenylcompounds represented by the formula (I) include:
6,10,14-trimethyl-3,5,9,13-pentadecatetraene-2-one
6,10,14-trimethyl-3,5-pentadenatetraene-2-one
6,10,14,18-tetramethyl-3,5,9,13,17-nonadecapentaene-2-one
6,10,14,18-tetramethyl-3,5,9,17-nonadecatetraene-2-one
6,10,14,18-tetramethyl-5,9,13,17-nonadecatetraene-2-one
6,10,14,18-tetramethyl-3,5-nonadecadiene-2-one
3,7,11,15-tetramethyl-2,6,10,14-hexadecatetraenoic acid
ethyl 3,7,11,15-tetramethyl-2,6,10,14-hexadecatetraenoate
3,7,11-trimethyl-2,4,6,10-dodecatetraenoic acid
ethyl 3,7,11-trimethyl-2,4,6,10-dodecatetraenoate
methyl 3,7,11,15-tetramethyl-2,4,6,10,14-hexadecapentaenoate.

Examples of the novel polyprenyl compounds represented by the formula (I) include:
3,7,11,15,19-pentamethyl-2,4,6,10,14,18-eicosahexaenoic acid
3,7,11,15-tetramethyl-2,4,6,14-hexadecatetraenoic acid
3,7,11,15-tetramethyl-2,4,6-hexadecatrienoic acid
3,7,11,15-tetramethyl-2,4,6,8,10,14-hexadecahexaenoic acid
3,7,11,15-tetramethyl-2,4,6,10-hexadecatetraenoic acid
3,7,11,15,19-pentamethyl-2,4,6,8,10,14,18-eicosaheptaenoic acid
3,7,11,15,19-pentamethyl-2,4,6,10,18-eicosapentaenoic acid
ethyl 3,7,11,15-tetramethyl-2,4,6-hexadecatrienoate ethyl 3,7,11,15,19-pentamethyl-2,4,6,10,14,18-eicosahexaenoate
methyl 3,7,11,15,19-pentamethyl-2,4,6,10,14,18-eicosahexaenoate
ethyl 3,7,11,15-tetramethyl-2,4,6,8,10,14-hexadecahexaenoate
3,7,11,15-tetramethyl-2,4,6,10,14-hexadecapentaenoamide
N-(p-hydroxyphenyl)-3,7,11,15-tetramethyl-2,4,6,10,14-hexadecapentaenoamide
N-ethyl-3,7,11,15-tetramethyl-2,4,6,10,14-hexadecapentaenoamide
N,N-dimethyl-3,7,11,15-tetramethyl-2,4,6,10,14-hexadecapentaenoamide
N-ethyl-3,7,11,15-tetramethyl-2,4,6,8,10,14-hexadecahexaenoamide
N-ethyl-3,7,11,15,19-pentamethyl-2,4,6,10,14,18-eicosahexaenoamide
ethyl 3,7,11,15-tetramethyl-2,4,6,10,14-hexadecapentaenoate
propyl 3,7,11,15-tetramethyl-2,4,6,10,14-hexadecapentaenoate
3,7,11,15-tetramethyl-6,10,14-hexadecatrienoic acid
N,N-dimethyl-3,7,11,15-tetramethyl-6,10,14-hexadecatrienoamide
N-ethyl-3,7,11,15-tetramethyl-2,6,10,14-hexadecatetraenoamide.

The novel polyrenyl compounds represented by the formula (I) such as exemplified as above can be prepared in the manner described in the aformentioned publications, in the process given hereinafter, or in the conventional manner.

The results of the pharmacological tests and toxicity tests on the polyprenyl compounds of the formula (I) are set forth below.

PHARMACOLOGICAL TESTS (ANTI-CANCER ACTIVITY)

(1) Test procedure

A mouse (ICR strain, female, 60 days age) was shaved at the back of the neck (to the extent to 5 cm$^2$). 7,12-Dimethylbenzo[2]-anthracene was dissolved in acetone to give 75 mg./100 ml. solution. The so prepared solution was applied to the mouse on the 60th aged day and further on the 75th aged day in the amount of 0.2 ml. per mouse.

Crotonic oil was dissolved in acetone to give 250 mg./100 ml. solution, and the so prepared solution was applied to the mouse in the amount of 0.2 ml. per mouse, twice a week until the treatment was started. When 3-7 papillomata (diameter of 3-8 mm. for each, and total diameter of 30-60 mm.) were produced for a mouse, the treatment was started.

The compound to be tested (test compound) was dissolved in groundnut oil to give 20 mg./ml. solution, and administered orally to the mouse. The solution was administered 10 times for 14 days (once a day), and the diameters of the papillomata were measured on the 14th day to determine the total diameter for each mouse. Ratio of increase or decrease of the papillomata was calculated from the total diameter on the 14th day and the total diameter measured prior to the starting of administration of the test compound. This value was adopted for evaluating the anti-cancer activity.

(2) Results

TABLE 1

| Test Compound | Number of Mice Tested | Ratio of increase or decrease of papillomata (%) |
| --- | --- | --- |
| Groundnut only (Control) | 3 | +17.1 |
| (1) COOH | 5 | −24.0 |
| (2) COOH | 4 | −19.5 |
| (3) COOC$_2$H$_5$ | 4 | −10.2 |
| (4) COOH | 5 | −26.3 |
| (5) CONHC$_2$H$_5$ | 5 | −25.5 |
| (6) COOC$_2$H$_5$ | 17 | −17.5 |
| (7) (ketone) | 5 | −12.7 |
| (8) COOH | 7 | −6.5 |

TABLE 1-continued

| Test Compound | Number of Mice Tested | Ratio of increase or decrease of papillomata (%) |
| --- | --- | --- |
| (9) [structure] | 7 | −8.2 |

Remarks:
The compounds identified by the structural formulae in Table 1 correspond to the following polyprenyl compounds.
(1) 3,7,11,15,19-pentamethyl-2,4,6,10,14,18-eicosahexaenoic acid
(2) 3,7,11,15-tetramethyl-2,4,6,14-hexadecatetraenoic acid
(3) ethyl 3,7,11,15-tetramethyl-2,4,6,14-hexadecatetraenoate
(4) 3,7,11,15-tetramethyl-2,4,6,8,10,14-hexadecahexaenoic acid
(5) —N—ethyl-3,7,11,15-tetramethyl-2,4,6,10,14-hexadecapentaeneamide
(6) ethyl 3,7,11,15-tetramethyl-2,4,6,10,14-hexadecapentaenoate
(7) 6,10,14,18-tetramethyl-3,5,9,13,17-nonadecapentaene-2-one
(8) 3,7,11,15-tetramethyl-2,6,10,14-hexadecatetraenoic acid
(9) 6,10,14,18-tetramethyl-5,9,13,17-nonadecatetraene-2-one As seen from the data in Table 1, the polyprenyl compounds of the formula (I) are effective against the papillomate.

TOXICITY TESTS (1) Test procedure

The test compound was administered repeatedly to a group of 6 mice (ICR strain, female) for 14 days in the dosage of 200 mg./kg./day. In the course of the administration procedures, increase or decrease of the weight of the mouse, occurrrence of death, etc. were observed.

(2) Test compound

The compounds set forth in the above Table 1 were employed.

(3) Test results

No death was observed. Decrease of the weight was not observed, and a little increase of the weight was observed. No symptoms indicating side effects, such as falling-out of hair, cyanosis, etc., were observed.

The decrease of the weight and the falling-out of hair are known as indicating the hypervitaminosis of Vitamin A. Accordingly, the results are considered to indicate that the polyprenyl compounds of the formula (I) do not cause the hypervitaminosis of Vitamin A.

In view of the pharmacological test results and the toxicity test results as described hereinbefore, the polyprenyl compounds of the formula (I) are judged to be of high safety and to be of value as anti-cancer agents for treatment of cancer and precancerous conditions.

It is well known that mouse papillomata as mentioned above are useful as a model for proliferous, allergic keratinization. Accordingly it is understood from the above shown data that the compound according to the invention is effective also on skin diseases with keratinization.

For the application of the anti-cancer agent, the polyprenyl compound of the formula (I) can be administered orally in the form of a powder, granules pellets, hard capsules, etc., or parenterally in the form of ointment, suppository, injection solution, etc. The dosage is generally set in the range of 40 mg. to 4 g./day for an adult. If the polyprenyl compound of the formula (I) is applied in the form of an external preparation, the dosage can be varied depending on the largeness of area of the affected part. The above-mentioned preparations can be prepared from the polyprenyl compound of the invention and generally employable carriers for the medical use by utilizing the conventional methods.

The following examples will illustrate processes for preparing the polyprenyl compounds of the formula (I) and the preparations comprising the polyprenyl compounds, but these examples are not given to restrict the present invention.

PREPARATION EXAMPLE 1

Ethyl 3,7,11,15-tetramethyl-2,4,6,14-hexadecatetraenoate

To a supsension of 2.5 g. of 55% sodium hydride (in oil) in 30 ml. of n-hexane was added 13.6 g. of triethyl phosphonoacetate. The mixture was then heated under reflux, and 10 g. of 6,10,14-trimethyl-3,5,13-pentadecatriene-2-one was added dropwise to the mixture under stirring. After 30 minutes, the reaction liquid was poured into 100 ml. of ice-water, and then 200 ml. of n-hexane was added for extraction. The n-hexane phase was separated, washed with two 50 ml. portions of a mixture of methanol and water (2:1), and concentrated. The so obtained concentrate was purified by the silica gel column chromatography to give 9.0 g. of the desired product as an oil.

| Analysis for $C_{22}H_{36}O_2$ | | |
| --- | --- | --- |
| | C | H |
| Calculated (%) | 79.46 | 10.92 |
| Found (%) | 79.74 | 11.04 |

NMR spectrum (δ, CDCl$_3$): 0.87 (3H, d, J=6 Hz), 1.28 (3H, t, J=7 Hz), 1.0–1.6 (7H), 161 (3H, s), 1.69 (3H, s), 1.85 (3H, s), 1.9–2.4 (4H), 23.4 (3H, d, J=1 Hz), 4.17 (2H, q, J=7 Hz), 5.10 (1H, t, J=7 Hz), 5.75 (1H, bs), 5.95 (1H, d, J=11 Hz), 6.16 (1H, d, J=15 Hz), 6.86 (1H, dd, J=15 Hz, 11 Hz).

Mass spectrum (m/e): 332 (M+).

PREPARATION EXAMPLE 2

3,7,11,15-Tetramethyl-2,4,6,14-hexadecatetraenoic acid 8.0 g. of the ethyl 3,7,11,15-tetramethyl-2,4,6,14-hexadecatetraenoate obtained in the previous Preparation Example 1 was added to a solution of 3.2 g. of potassium hydroxide in 20 ml. of isopropyl alcohol, and the mixuture was stirred at 50° C. for 1 hour. The reaction liquid was then poured into ice-water, made acidic by addition of hydrochloric acid, and extracted with 50 ml. of diethyl ether. The ether phase was washed with water, dried over magnesium sulfate, and concentrated to give 7. g. of an oil. The oil was dissolved in 40 ml. of n-hexane and crystallized at −20° C. to give 3.1 g. of the desired product as white crystals.

M.p.: 60°–62° C.

| Analysis for $C_{20}H_{32}O_2$ | | |
|---|---|---|
| | C | H |
| Calculated (%) | 78.89 | 10.59 |
| Found (%) | 78.77 | 10.63 |

NMR spectrum (δ, CDCl₃): 0.87 (3H, d, J=6 Hz), 1.0–1.6 (7H), 1.60 (3H, s), 1.69 (3H, s), 1.85 (3H, s) 1.9–2.3 (4H), 2.34 (3H, d, J=1 Hz), 5.10 (1H, t, J=7 Hz), 5.77 (1H, bs), 5.97 (1H, d, J=11 Hz), 6.20 (1H, d, J=15 Hz), 6.91 (1H, dd, J=15 Hz, 11 Hz), 9.6 (1H, b).

Mass spectrum (m/e): 304 (M+).

PREPARATION EXAMPLE 3

3,7,11,15-Tetramethyl-2,4,6,8,10,14-hexadecahexaenoic acid

To a suspension of 30.3 g. of sodium ethoxide in 300 ml. of tetrahydrofuran was added 118 g. of diethyl 3-ethoxycarbonyl-2-methyl-2-propenylphosphonate. To the mixture was added 67 g. of 3,7,11-trimethyl-2,4,6,10-dodecatetraene-1-ol under stirring, chilling with ice and shielding from the light. After 1 hour, the reaction liquid was poured into 1 liter of water, and 1 liter of n-hexane was added for extraction. The n-hexane phase was separated, washed with two 100 ml. portions of a mixture of methanol and water (2:1), and concentrated to give 99 g. of a concentrate. To a refluxing solution of 8.2 g. of potassium hydroxide and 80 ml. of isopropyl alcohol was added 21 g. of the concentrate under shielding from the light. After 15 minutes, the reaction liquid was poured into 300 ml. of ice-water, made acidic by addition of hydrochloric acid, and extracted with 300 ml. of diethyl ether. The extract was washed with three 100 ml. portions of water, dried over magnesium sulfate, and evaporated to remove the solvent. The residue was dissolved in 200 ml. of n-hexane and chilled to −20° C. to crystallize it. There was obtained 9.8 g. of the desired product as pale yellow crystals.

| Analysis for $C_{20}H_{28}O_2$ | | |
|---|---|---|
| | C | H |
| Calculated (%) | 79.95 | 9.39 |
| Found (%) | 80.22 | 9.47 |

NMR spectrum (δ, CDCl₃): 1.63 (3H, s), 1.69 (3H, s), 1.84 (3H, s), 1.99 (3H, s), 2.0–2.3 (4H), 2.36 (3H, s), 5.15 (1H, m), 5.6–7.2 (7H, m), 1.04 (1H, b).

Mass spectrum (m/e): 300 (M+).

PREPARATION EXAMPLE 4

3,7,11,15,19-Pentamethyl-2,4,6,10,14,18-eicosahexaenoic acid

In 100 ml. of tetrahydrofuran was dissolved 12 g. of 1-p-tolylsulfonyl-3,7,11,15-tetramethyl-2,6,10,14-hexadecatetraene, and the solution was chilled to −50° C. To the solution was added dropwise 18.5 ml. of 15% n-butyllithium-n-hexane solution under stirring and in a stream of nitrogen, maintaining the temperature of the solution at −50° C. Then, 300 ml. of tetrahydrofuran solution containing 5.7 g. of ethyl 4-bromo-3-methyl-2-butenate was added dropwise to the so produced solution. After 30 minutes, 100 ml. of 10% aqueous ammonium chloride solution was added, and then the mixture was allowed to stand to reach room temperature. The mixture was subsequently extracted with two 200 ml. portions of n-hexane. The n-hexane phase was washed with three 100 ml. portions of water, dried over magnesium sulfate, and evaporated to remove the solvent. There was obtained 14 g. of ethyl 3,7,11,15,19-pentamethyl-5-p-tolylsulfonyl-2,6,10,14,18-eicosapentaenoate.

To 4.1 g. of potassium hydroxide in 50 ml. of isopropyl alcohol was added 12 g. of the above-obtained ethyl 3,7,11,15,19-pentamethyl-5-p-tolylsulfonyl-2,6,10,14,18-eicosapentaenoate, and the mixture was stirred at 50° C. for 3 hours. The reaction liquid was poured into ice-water, made acidic by addition of hydrochloric acid, and extracted with 100 ml. of diethyl ether. The extract was washed with water, dried over magnesium sulfate and evaporated to remove the solvent. There was obtained 8.5 g. of an oil. The so obtained oil was dissolved in 40 ml. of n-hexane and chilled to −20° C. to crystallize it. There was obtained 2.3 g. of the desired product as white crystals.

M.p.: 45.5°–46.5° C.

| Analysis for $C_{25}H_{38}O_2$ | | |
|---|---|---|
| | C | H |
| Calculated (%) | 81.03 | 10.34 |
| Found (%) | 80.89 | 10.52 |

NMR spectrum (δ, CDCl₃): 1.60 (9H, s), 1.68 (3H, s), 1.86 (3H, s), 1.9–2.3 (12H), 2.33 (3H, s), 5.09 (3H, b), 5.76 (1H, bs), 5.96 (1H, d, J=10 Hz), 6.18 (1H, d, J=15 Hz), 6.89 (1H, dd, J=15 Hz, 10 Hz), 10.2 (1H, b).

Mass spectrum (m/e): 370 (M+).

PREPARATION EXAMPLE 5

Ethyl 3,7,11,15-tetramethyl-2,4,6-hexadecatrienoate

The procedures described in Preparation Example 1 were repeated using 6,10,14-trimethyl-3,5-pentadecadiene-2-one to obtain the desired product as an oil.

| Analysis for $C_{22}H_{38}O_2$ | | |
|---|---|---|
| | C | H |
| Calculated (%) | 78.98 | 11.45 |
| Found (%) | 79.16 | 11.56 |

NMR spectrum (δ, CDCl₃): 0.87 (9H, d, J=7 Hz), 1.27 (3H, t, J=7 Hz), 0.9–1.6 (12H), 1.84 (3H, s), 2.08 (2H, t, J=7 Hz), 2.34 (3H, s), 4.16 (2H, q, J=7 Hz), 5.74 (1H, bs), 5.95 (1H, d, J=11 Hz), 6.16 (1H, d, J=15 Hz), 6.85 (1H, dd, J=15 Hz, 11 Hz).

Mass spectrum (m/e): 334 (M+).

PREPARATION EXAMPLE 6

3,7,11,15-Tetramethyl-2,4,6-hexadecatrienoic acid

The procedures described in Prepration Example 2 were repeated using the ethyl 3,7,11,15-tetramethyl-2,4,6-hexadecatrienoate obrained in Preparation Example 5 to carry out the hydrolysis. There was obtained the desired product as white crystals.

M.p.: 84.5°–85.5° C.

| Analysis for $C_{20}H_{34}O_2$ | | |
|---|---|---|
| | C | H |
| Calculated (%) | 78.38 | 11.18 |
| Found (%) | 78.35 | 11.21 |

NMR spectrum (δ, CDCl$_3$): 0.87 (9H, d, J=7 Hz), 0.9–1.6 (12H), 1.84 (3H, s), 2.09 (2H, t, J=7 Hz), 2.35 (3H, s), 5.76 (1H, bs), 5.96 (1H, d, J=11 Hz), 6.19 (1H, d, J=15 Hz), 6.90 (1H, dd, J=15 Hz, 11 Hz), 11.5 (1H, b).

Mass spectrum (m/e): 306 (M+).

PREPARATION EXAMPLE 7

Ethyl 3,7,11,15-tetramethyl-2,4,6,10,14-hexadecapentaenoate

To a suspension of 5.0 g. of 55% sodium hydride (in oil) in 60 ml. of n-hexane was added 28.6 g. of triethyl phosphonoacetate. The mixture was then heated under reflux, and 20 g. of 6,10,14-trimethyl-3,5,9,13-pentadecatetraene was added dropwise to the mixture under stirring. After 30 minutes, the reaction liquid was poured into 200 ml. of ice-water, and then 500 ml. of n-hexane was added for extraction. The n-hexane phase was separated, washed with two 100 ml. portions of a mixture of methanol and water (2:1), and concentrated. The so obtained concentrate was purified by silica gel column chromatography to give 18 g. of the desired product as an oil.

| Analysis for C$_{22}$H$_{34}$O$_2$ | | |
|---|---|---|
| | C | H |
| Calculated (%) | 79.95 | 10.37 |
| Found (%) | 80.11 | 10.26 |

NMR spectrum (δ, CDCl$_3$): 1.28 (3H, t, J=7 Hz), 1.60 (6H, s), 1.68 (3H, s), 1.85 (3H, s), 1.9∝2.3 (8H), 2.33 (3H, d, J=1 Hz), 4.16 (2H, q, J=7 Hz), 5.09 (2H, b), 5.73 (1H, bs), 5.96 (1H, d, J=11 Hz), 6.16 (1H, d, J=15 Hz), 6.85 (1H, dd, J=15 Hz, 11 Hz).

Mass spectrum (m/e): 330 (M+).

PREPARATION EXAMPLE 8

3,7,11,15-Tetramethyl-2,4,6,10,14-hexadecapentaenoamide

To 3.9 g. of potassium hydroxide in 30 ml. of isopropyl alcohol was added 10 g. of the ethyl 3,7,11,15-tetramethyl-2,4,6,10,14-hexadecapentaenoate obtained in Preparation Example 7, and the mixture was stirred at 50° C. for 1 hour. The reaction liquid was poured into ice-water, made acidic by addition of hydrochloric acid, and extracted with 100 ml. of diethyl ether. The ether phase was washed with water, dried over magnesium sulfate and concentrated to give 9.0 g. of an oil. The so obtained oil was dissolved in 50 ml. of n-hexane and chilled to −20° C. to crystallize it. There was obtained 4.0 g. of 3,7,11,15-tetramethyl-2,4,6,10,14-hexadecapentaenoic acid as pale yellow needles.

In 20 ml. of diethyl ether was dissolved 3.0 g. of the above-obtained 3,7,11,15-tetramethyl-2,4,6,10,14-hexadecapentaenoic acid. To this solution was added 1 g. of triethylamine, and further added 1.1 g. of ethyl chlorocarbonate under stirring at room temperature. After 10 minutes, gaseous ammonia was introduced into the solution. The reaction liquid was washed with three 10 ml. portions of water, dried over magnesium sulfate, and evaporated to remove the solvent. The residue was purified by alumina column chromatography and crystallized from a mixture of acetone and n-hexane (1:2). There was obtained 1.7 g. of the desired product as pale yellow crystals.

M.p.: 63°–65° C.

| Analysis for C$_{20}$H$_{31}$NO | | | |
|---|---|---|---|
| | C | H | N |
| Calculated (%) | 79.67 | 10.37 | 4.65 |
| Found (%) | 79.48 | 10.59 | 4.73 |

NMR spectrum (δ, CDCl$_3$): 1.60 (6H, s), 1.68 (3H, s), 1.84 (3H, d, J=1 Hz), 1.9–2.3 (8H), 2.33 (3H, d, J=1 Hz), 5.08 (2H, m), 5.70 (1H, bs), 5.4–6.1 (2H, b), 5.95 (1H, d, J=11 Hz), 6.15 (1H, d, J=15 Hz), 6.82 (1H, dd, J=15 Hz, 11 Hz).

Mass spectrum (m/e): 301 (M+).

PREPARATION EXAMPLE 9

N-(p-Hydroxyphenyl)-3,7,11,15-tetramethyl-2,4,6,10,14-hexadecapentaenoamide

In 30 ml. of tetrahydrofuran was dissolved 3 g. of 3,7,11,15-tetramethyl-2,4,6,10,14-hexadecapentaneoic acid. To this solution was added 1 g. of triethylamine, and further added 1.1 g. of ethyl chlorocarbonate under stirring at room temperature. After 10 minutes, the reaction liquid was poured into 100 ml. of water, and extracted with 100 ml. of n-hexane. The extract was washed with 50 ml. of water and evaporated to remove the solvent. The residue was dissolved in 30 ml. of tetrahydrofuran. To this solution was added 1.1 g. of p-aminophenol, and the mixture was stirred at room temperature for 30 minutes. To the reaction liquid was added 200 ml. of diethyl ether, and the mixture was washed successively with two 50 ml. portions of dilute hydrochloric acid and two 50 ml. portions of water. The ether phase was dried over magnesium sulfate and evaporated to remove the solvent. The residue was crystallized from ethanol to obtain 3.2 g. of the desired product as pale yellow crystals.

M.p.: 163°–164° C.

| Analysis for C$_{26}$H$_{35}$NO$_2$ | | | |
|---|---|---|---|
| | C | H | N |
| Calculated (%) | 79.34 | 8.96 | 3.56 |
| Found (%) | 79.61 | 8.78 | 3.62 |

NMR spectrum (δ, CDCl$_3$): 1.61 (6H, s), 1.68 (3H, s), 1.85 (3H, s), 1.9–2.3 (8H), 2.38 (3H, s), 5.09 (2H, m), 5.76 (1H, bs), 5.96 (1H, d, J=11 Hz), 6.15 (1H, d, J=15 Hz), 6.42 (1H, b), 6.74 (2H, d, J=8 Hz), 6.82 (1H, d, J=15 Hz, 11 Hz), 7.22 (1H, bs), 7.32 (2H, d, J=8 Hz).

Mass spectrum (m/e): 393 (M+).

PREPARATION EXAMPLE 10

N-Ethyl-3,7,11,15-tetramethyl-2,4,6,10,14-hexadecapentaenoamide 3,7,11,15-Tetramethyl-2,4,6,10,14-hexadecapentaenoic acid and ethylamine were reacted in the same manner as in Preparation Example 9 to obtain the desired product as an oil.

| Analysis for C$_{22}$H$_{35}$NO | | | |
|---|---|---|---|
| | C | H | N |
| Calculated (%) | 80.19 | 10.71 | 4.25 |
| Found (%) | 80.44 | 10.79 | 4.38 |

NMR spectrum (δ, CDCl$_3$): 1.15 (3H, t, J=7 Hz), 1.60 (6H, s), 1.67 (3H, s), 1.83 (3H, s), 1.9–2.3 (8H), 2.33

(3H, d, J=1 Hz), 3.27 (2H, qd, J=7 Hz, 6 Hz), 5.10 (2H, m), 5.65 (1H, bs), 5.82 (1H, t, J=6 Hz), 5.94 (1H, d, J=11 Hz), 6.10 (1H, d, J=15 Hz), 6.77 (1H, dd, J=15 Hz, 11 Hz).

Mass spectrum (m/e): 329 (M+).

PREPARATION EXAMPLE 11

N,N-Dimethyl-3,7,11,15-tetramethyl-2,4,6,10,14-hexadecapentaenoamide 3,7,11,15-Tetramethyl-2,4,6,10,14-hexadecapentaenoic acid and dimethylamine were reacted in the same manner as in Preparation Example 9 to obtain the desired product as pale yellow crystals.

M.p.: 39°–39.5° C.

| Analysis for $C_{22}H_{35}NO$ | | | |
|---|---|---|---|
| | C | H | N |
| Calculated (%) | 80.19 | 10.71 | 4.25 |
| Found (%) | 80.26 | 10.83 | 4.32 |

NMR spectrum (δ, CDCl₃): 1.60 (6H, s), 1.68 (3H,s), 1.76 (3H, s), 2.09 (3H, d, J=1 Hz), 1.9–2.3 (8H), 3.00 (3H, s), 3.01 (3H, s), 5.10 (2H, m), 5.93 (1H, bs), 5.94 (1H, d, J=10 Hz), 6.18 (1H, d, J=15 Hz), 6.68 (1H, dd, J=15 Hz, 10 Hz).

Mass spectrum (m/e): 329 (M+).

EXAMPLE 1

| Tablet Preparation | |
|---|---|
| N—Ethyl-3,7,11,15-tetramethyl-2,4,6,10,14-hexadecapentaenoamide | 50 g. |
| Silicic anhydride | 30 g. |
| Crystalline cellulose | 50 g. |
| Corn starch | 36 g. |
| Hydroxypropylcellulose | 10 g. |
| Magnesium stearate | 4 g. |

The above-described composition was processed in the conventional manner to produce tablets (180 mg. per one tablet).

We claim:

1. A method for reducing the size of papillomata in a subject suffering from papillomata which comprises administering to said subject an effective dosage of a polyprenyl compound having the formula (I):

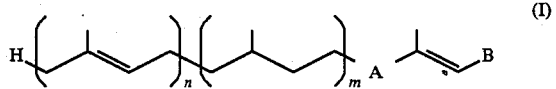

in which each of n and m is 0, 1 or 2, n+m is 0, 1 or 2, A is

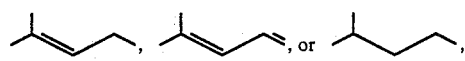

and B is

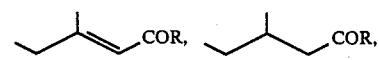

-continued

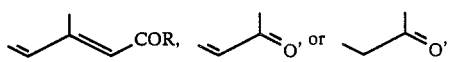

wherein R is hydroxy, lower alkoxy, or

in which each of $R_1$ and $R_2$ is hydrogen, lower alkyl or aryl; with the proviso that R is lower alkoxy or

when n is 1, m is 0, A is

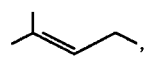

and B is

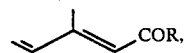

said dosage being therapeutically effective to reduce the size of papillomata in said subject.

2. A method as claimed in claim 1 in which said polyprenyl compound is 3,7,11,15,19-pentamethyl-2,4,6,10,14,18-eicosahexaenoic acid.

3. A method as claimed in claim 1 in which said polyprenyl compound is 3,7,11,15-tetramethyl-2,4,6,10,14-hexadecatetraenoic acid.

4. A method as claimed in claim 1 in which said polyprenyl compound is ethyl 3,7,11,15-tetramethyl-2,4,6,14-hexadecatetraenoate.

5. A method as claimed in claim 1 in which said polyprenyl compound is 3,7,11,15-tetramethyl-2,4,6,8,10,14-hexadecahexaenoic acid.

6. A method as claimed in claim 1 in which said polyprenyl compound is N-ethyl-3,7,11,15-tetramethyl-2,4,6,10,14-hexadecapentaeneamide.

7. A method as claimed in claim 1 in which said polyprenyl compound is ethyl 3,7,11,15-tetramethyl-2,4,6,10,14-hexadecapentaenoate.

8. A method as claimed in claim 1 in which said polyprenyl compound is 6,10,14,18-tetramethyl-3,5,9,13,17-nonadecapentaene-2-one.

9. A method as claimed in claim 1 in which said polyprenyl compound is 3,7,11,15-tetramethyl-2,6,10,14-hexadecatetraenoic acid.

10. A method as claimed in claim 1 in which said polyprenyl compound is 6,10,14,18-tetramethyl-5,9,13,17-nonadecatetraene-2-one.

11. A method as claimed in claim 1, wherein said polyprenyl compound is orally or parenterally administered to a human patient suffering from papillomata in a dosage ranging from 40 mg to 4 g/day, for an adult human being.

* * * * *